US007285245B2

(12) United States Patent
Seto

(10) Patent No.: US 7,285,245 B2
(45) Date of Patent: Oct. 23, 2007

(54) BIOCHEMICAL ANALYSIS METHOD AND APPARATUS

(75) Inventor: Yoshihiro Seto, Kaisei-machi (JP)

(73) Assignee: Fujifilm Corporation, Tokyo (JP)

( * ) Notice: Subject to any disclaimer, the term of this patent is extended or adjusted under 35 U.S.C. 154(b) by 386 days.

(21) Appl. No.: 10/233,554

(22) Filed: Sep. 4, 2002

(65) Prior Publication Data

US 2003/0044990 A1   Mar. 6, 2003

(30) Foreign Application Priority Data

Sep. 5, 2001 (JP) .............................. 2001-269280
Sep. 5, 2001 (JP) .............................. 2001-269281

(51) Int. Cl.
   *G01N 21/00*   (2006.01)

(52) U.S. Cl. .......................... 422/65; 422/63; 422/64; 422/99; 422/100; 436/46; 436/47; 436/48; 436/180

(58) Field of Classification Search .................. 436/63, 436/64, 46–48, 180; 422/99–101, 63–65
See application file for complete search history.

(56) References Cited

U.S. PATENT DOCUMENTS 4,855,110 A * 8/1989 Marker et al. .............. 422/102
5,219,526 A * 6/1993 Long ............................ 422/64
6,267,927 B1 * 7/2001 Pomar Longedo et al. ... 422/65

FOREIGN PATENT DOCUMENTS

EP   0458138 A1   11/1991

* cited by examiner

*Primary Examiner*—Jill Warden
*Assistant Examiner*—Jyoti Nagpaul
(74) *Attorney, Agent, or Firm*—Sughrue Mion, PLLC

(57) ABSTRACT

Samples and dry chemical analysis elements necessary for analyses of the samples are loaded on a circular sampler tray. Each of the samples having been loaded on the sampler tray is sucked through a spotting nozzle and spotted onto one of the dry chemical analysis elements. A temperature of each of the dry chemical analysis elements having been spotted with the samples is kept at a constant temperature in an incubator. The sampler tray is provided with a circular rotating disk. Sample vessels, each of which accommodates one of the samples, the dry chemical analysis elements of kinds corresponding to types of the analyses of the samples, nozzle tips, each of which is to be fitted to the spotting nozzle, diluent liquid vessels accommodating a diluent liquid, and mixing cups for dilution are supported on the rotating disk.

7 Claims, 6 Drawing Sheets

BIOCHEMICAL ANALYSIS METHOD AND APPARATUS

BACKGROUND OF THE INVENTION

1. Field of the Invention

This invention relates to a biochemical analysis method and apparatus, wherein a sample, such as blood or urine, is spotted onto a dry chemical analysis element, such as a colorimetric-type dry chemical analysis element or an electrolyte-type dry chemical analysis element, by use of a spotting nozzle unit, and a substance concentration of a specific biochemical substance contained in the sample, an ionic activity of a specific ion contained in the sample, or the like, is determined.

2. Description of the Related Art

Colorimetric-type dry chemical analysis elements and electrolyte-type dry chemical analysis elements have heretofore been used in practice. When a droplet of a sample is merely spotted onto the colorimetric-type dry chemical analysis element, a specific chemical constituent or a specific physical constituent contained the sample is capable of being analyzed quantitatively. Also, when a droplet of a sample is merely spotted onto the electrolyte-type dry chemical analysis element, an ionic activity of a specific ion contained the sample is capable of being analyzed quantitatively. Biochemical analysis apparatuses utilizing the dry chemical analysis elements are capable of performing sample analyses easily and quickly and have therefore been utilized widely in medical facilities, medical laboratories, and the like.

Colorimetry utilizing colorimetric-type dry chemical analysis elements is performed in the manner described below. Specifically, after a sample has been spotted onto a dry chemical analysis element, the dry chemical analysis element having been spotted with the sample is kept at a constant temperature for a predetermined time within an incubator and is thereby caused to undergo a color reaction (i.e., a dye forming reaction). Thereafter, measuring light, which has wavelengths selected previously in accordance with a combination of a predetermined biochemical substance contained in the sample and a reagent contained in the dry chemical analysis element, is irradiated to the dry chemical analysis element, and an optical density of the dry chemical analysis element is thereby measured. The concentration of the predetermined biochemical substance contained in the sample is determined from the measured optical density and by use of a calibration curve having been formed previously, which represents a correspondence relationship between the optical density and the substance concentration of the predetermined biochemical substance.

Potentiometry utilizing electrolyte-type dry chemical analysis elements is performed in the manner described below. Specifically, in lieu of the optical density described above being measured, the ionic activity of a specific ion contained in a sample, which has been spotted onto an electrode pair comprising a pair of two dry type ion selective electrodes of an identical type, is determined through quantitative analysis with potentiometry by use of a reference liquid.

In each of the colorimetry and the potentiometry described above, the liquid-state sample is accommodated in a sample vessel (such as a blood-collecting tube), and the sample vessel accommodating the sample is set on a biochemical analysis apparatus. Also, the dry chemical analysis element necessary for the measurement is fed into the biochemical analysis apparatus. Further, by the utilization of a spotting nozzle unit comprising a spotting nozzle, which is capable of being moved in a predetermined direction, the sample is sucked up from the sample vessel and spotted onto the dry chemical analysis element having been conveyed to the position for spotting. Various techniques have heretofore been proposed for the loading of the sample, the dry chemical analysis element, a plurality of nozzle tips acting as expendables for the measurement, a mixing cup for dilution, a diluent liquid, a reference liquid, and the like, into the biochemical analysis apparatus.

From the view point of efficiency and operability, the biochemical analysis apparatus described above should preferably be constituted such that the biochemical analysis apparatus is capable of being loaded with a plurality of samples and is capable of performing the analyses successively. However, in such cases, the problems have heretofore occurred in that the size of the biochemical analysis apparatus cannot be kept small.

SUMMARY OF THE INVENTION

The primary object of the present invention is to provide a biochemical analysis method, wherein biochemical analyses are capable of being performed efficiently with a small biochemical analysis apparatus by loading a plurality of samples, a plurality of dry chemical analysis elements corresponding to types of the analyses of samples, and expendables, such as nozzle tips, on the biochemical analysis apparatus.

Another object of the present invention is to provide a biochemical analysis method, wherein a sample feeding path is set specifically with respect to an element conveyance path along which each of dry chemical analysis elements is conveyed, and biochemical analyses are capable of being performed with a biochemical analysis apparatus having a small size.

The specific object of the present invention is to provide a biochemical analysis apparatus for carrying out the biochemical analysis method.

The present invention provides a first biochemical analysis method, comprising the steps of:

i) loading a plurality of samples and a plurality of dry chemical analysis elements, which are necessary for analyses of the samples, on a circular sampler tray, ii) sucking each of the samples, which have been loaded on the sampler tray, with a spotting nozzle unit, iii) spotting the sucked sample onto one of the dry chemical analysis elements with the spotting nozzle unit, and iv) keeping a temperature of each of the dry chemical analysis elements, which have been spotted with the samples, at a constant temperature in an incubator, wherein the sampler tray is provided with a circular rotating disk, and a plurality of sample vessels, each of which accommodates one of the samples, the plurality of the dry chemical analysis elements, which are of kinds corresponding to types of the analyses of the samples, a plurality of nozzle tips, each of which is to be fitted to a spotting nozzle of the spotting nozzle unit, a plurality of diluent liquid vessels, which accommodate a diluent liquid, and a plurality of mixing cups for dilution are supported on the rotating disk.

The first biochemical analysis method in accordance with the present invention should preferably be modified such that the sampler tray is provided with a non-rotating section, which is located at a center region of the sampler tray, a reference liquid vessel, which accommodates a reference liquid, is supported in the non-rotating section, and an evaporation preventing cover, which opens and closes an opening of the reference liquid vessel, is located in the non-rotating section.

In such cases, the evaporation preventing cover should preferably undergo opening and closing operations in accordance with movements of the spotting nozzle.

Also, the first biochemical analysis method in accordance with the present invention should preferably be modified such that an element conveying member is located within the sampler tray, the element conveying member pushing each of the dry chemical analysis elements from a center side of the rotating disk and thereby conveying each of the dry chemical analysis elements, and the rotating disk is provided with a path for the element conveying member besides sections for supporting the plurality of the dry chemical analysis elements.

The present invention also provides a second biochemical analysis method, comprising the steps of:

i) loading a plurality of samples and a plurality of dry chemical analysis elements, which are necessary for analyses of the samples, on a circular sampler tray, ii) sucking each of the samples, which have been loaded on the sampler tray, through a spotting nozzle of a spotting nozzle unit, iii) spotting the sucked sample onto one of the dry chemical analysis elements from the spotting nozzle of the spotting nozzle unit, and iv) keeping a temperature of each of the dry chemical analysis elements, which have been spotted with the samples, at a constant temperature in an incubator, wherein an element conveyance path, along which each of the dry chemical analysis elements is conveyed from the sampler tray to a spotting section for the sample spotting, and a spotting nozzle movement path, along which the spotting nozzle of the spotting nozzle unit is moved, are set on an identical straight line.

The second biochemical analysis method in accordance with the present invention should preferably be modified such that a tip scrapping section for removing a nozzle tip, which has been fitted to the spotting nozzle, from the spotting nozzle is located on an extension of the element conveyance path, and the nozzle tip, which has been removed from the spotting nozzle at the tip scrapping section, is allowed to fall so as to pass through a plane of conveyance of the dry chemical analysis element and is scrapped.

The present invention further provides a first biochemical analysis apparatus, comprising:

i) a circular sampler tray, which is capable of being loaded with a plurality of samples and a plurality of dry chemical analysis elements necessary for analyses of the samples, ii) a spotting nozzle unit for sucking each of the samples, which have been loaded on the sampler tray, and spotting the sucked sample onto one of the dry chemical analysis elements, and iii) an incubator for keeping a temperature of each of the dry chemical analysis elements, which have been spotted with the samples, at a constant temperature, wherein the sampler tray is provided with a circular rotating disk, and the rotating disk is provided with:

a plurality of loading sections for supporting a plurality of sample vessels, each of which accommodates one of the samples, a plurality of loading sections for supporting the plurality of the dry chemical analysis elements, which are of kinds corresponding to types of the analyses of the samples, at least one loading section for supporting a plurality of nozzle tips, each of which is to be fitted to a spotting nozzle of the spotting nozzle unit, at least one loading section for supporting a plurality of diluent liquid vessels, which accommodate a diluent liquid, and at least one loading section for supporting a plurality of mixing cups for dilution.

The first biochemical analysis apparatus in accordance with the present invention should preferably be modified such that the sampler tray is provided with a non-rotating section, which is located at a center region of the sampler tray, and the non-rotating section is provided with:

a reference liquid loading section for supporting a reference liquid vessel, which accommodates a reference liquid, and an evaporation preventing cover, which opens and closes an opening of the reference liquid vessel.

In such cases, the evaporation preventing cover should preferably undergo opening and closing operations in accordance with movements of the spotting nozzle.

Also, the first biochemical analysis apparatus in accordance with the present invention should preferably be modified such that an element conveying member is located within the sampler tray, the element conveying member pushing each of the dry chemical analysis elements from a center side of the rotating disk and thereby conveying each of the dry chemical analysis elements, and the rotating disk is provided with a path for the element conveying member besides the loading sections for supporting the plurality of the dry chemical analysis elements.

The present invention still further provides a second biochemical analysis apparatus, comprising:

i) a circular sampler tray, which is capable of being loaded with a plurality of samples and a plurality of dry chemical analysis elements necessary for analyses of the samples, ii) a spotting nozzle unit for sucking each of the samples, which have been loaded on the sampler tray, through a spotting nozzle, and spotting the sucked sample onto one of the dry chemical analysis elements, and iii) an incubator for keeping a temperature of each of the dry chemical analysis elements, which have been spotted with the samples, at a constant temperature, wherein an element conveyance path, along which each of the dry chemical analysis elements is conveyed from the sampler tray to a spotting section for the sample spotting, and a spotting nozzle movement path, along which the spotting nozzle of the spotting nozzle unit is moved, are set on an identical straight line.

The second biochemical analysis apparatus in accordance with the present invention should preferably be modified such that a tip scrapping section for removing a nozzle tip, which has been fitted to the spotting nozzle, from the spotting nozzle is located on an extension of the element conveyance path, and the nozzle tip, which has been removed from the spotting nozzle at the tip scrapping section, is allowed to fall so as to pass through a plane of conveyance of the dry chemical analysis element and is scrapped.

With the first biochemical analysis method and the first biochemical analysis apparatus in accordance with the present invention, the sampler tray is provided with the circular rotating disk. The rotating disk is loaded with the plurality of the sample vessels, each of which accommodates one of the samples, the plurality of the dry chemical analysis elements, which are of the kinds corresponding to the types of the analyses of the samples, the plurality of the nozzle tips, each of which is to be fitted to the spotting nozzle of the spotting nozzle unit, the plurality of the diluent liquid vessels, which accommodate a diluent liquid, and the plurality of the mixing cups for dilution. Therefore, with the first biochemical analysis method and the first biochemical analysis apparatus in accordance with the present invention, the biochemical analyses are capable of being performed efficiently by loading the plurality of the samples, the plurality of the dry chemical analysis elements corresponding to the types of the analyses of the samples, expendables, such as the nozzle tips, and the like, on the biochemical analysis apparatus. Accordingly, burden to an operator is capable of being kept light, and the size of the biochemical analysis apparatus is capable of being kept small.

With the first biochemical analysis method and first biochemical analysis apparatus in accordance with the present invention, the sampler tray may be provided with the non-rotating section, which is located at the center region of the sampler tray, and the reference liquid loading section may be located at the non-rotating section. Also, the evaporation preventing cover, which opens and closes the opening of the reference liquid vessel, may be located at the non-rotating section. In such cases, a mechanism for interlocking the opening and closing operations of the evaporation preventing cover with the operations of the spotting nozzle unit is capable of being constituted easily.

With the second biochemical analysis method and the second biochemical analysis apparatus in accordance with the present invention, the element conveyance path, along which each of the dry chemical analysis elements is conveyed from the sampler tray to the spotting section for the sample spotting, and the spotting nozzle movement path, along which the spotting nozzle of the spotting nozzle unit is moved, are set on an identical straight line. Therefore, sections constituting the biochemical analysis apparatus are located so as to overlap one upon another in three dimensions. In particular, the width of the biochemical analysis apparatus, which width is taken in the direction normal to the element conveyance path, is capable of being kept small. Accordingly, the size of the entire biochemical analysis apparatus is capable of being kept small.

With the second biochemical analysis method and the second biochemical analysis apparatus in accordance with the present invention, the tip scrapping section for removing the nozzle tip, which has been fitted to the spotting nozzle, from the spotting nozzle may be located on an extension of the element conveyance path, and the nozzle tip, which has been removed from the spotting nozzle at the tip scrapping section, may be allowed to fall so as to pass through the plane of conveyance of the dry chemical analysis element and may thus be scrapped. In such cases, the tip scrapping section is capable of being located such that the size of the biochemical analysis apparatus may be kept small.

Further, with the second biochemical analysis method and the second biochemical analysis apparatus in accordance with the present invention, the spotting nozzle unit may be moved along the straight line and over a shortest possible distance. Therefore, the analyses are capable of being made quickly.

DESCRIPTION OF THE PREFERRED EMBODIMENTS

The present invention will herein below be described in further detail with reference to t he accompanying drawings.

Figure 1:
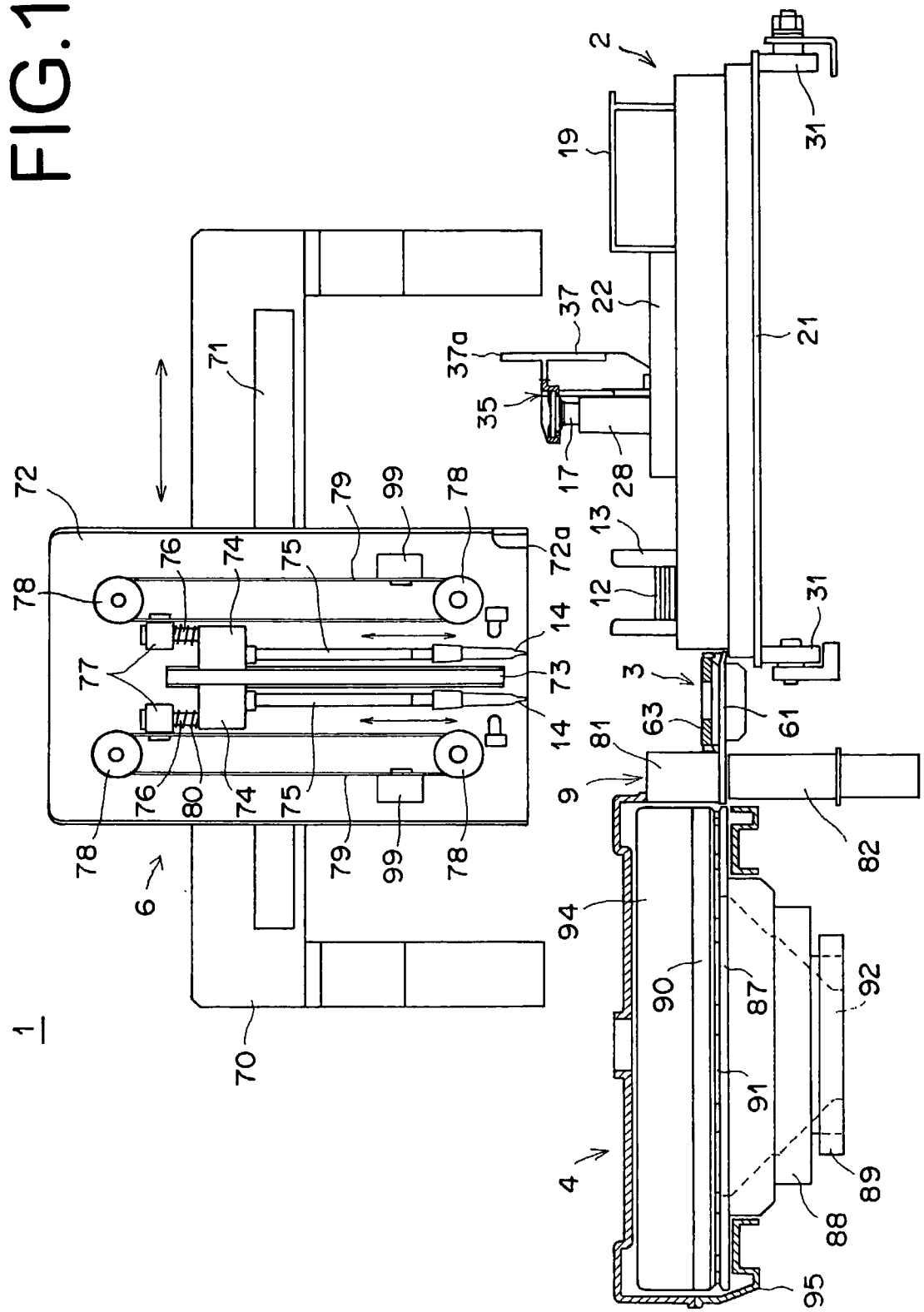
FIG. 1 is a partially sectional front view showing an embodiment of the biochemical analysis apparatus in accordance with the present invention.
Figure 2:
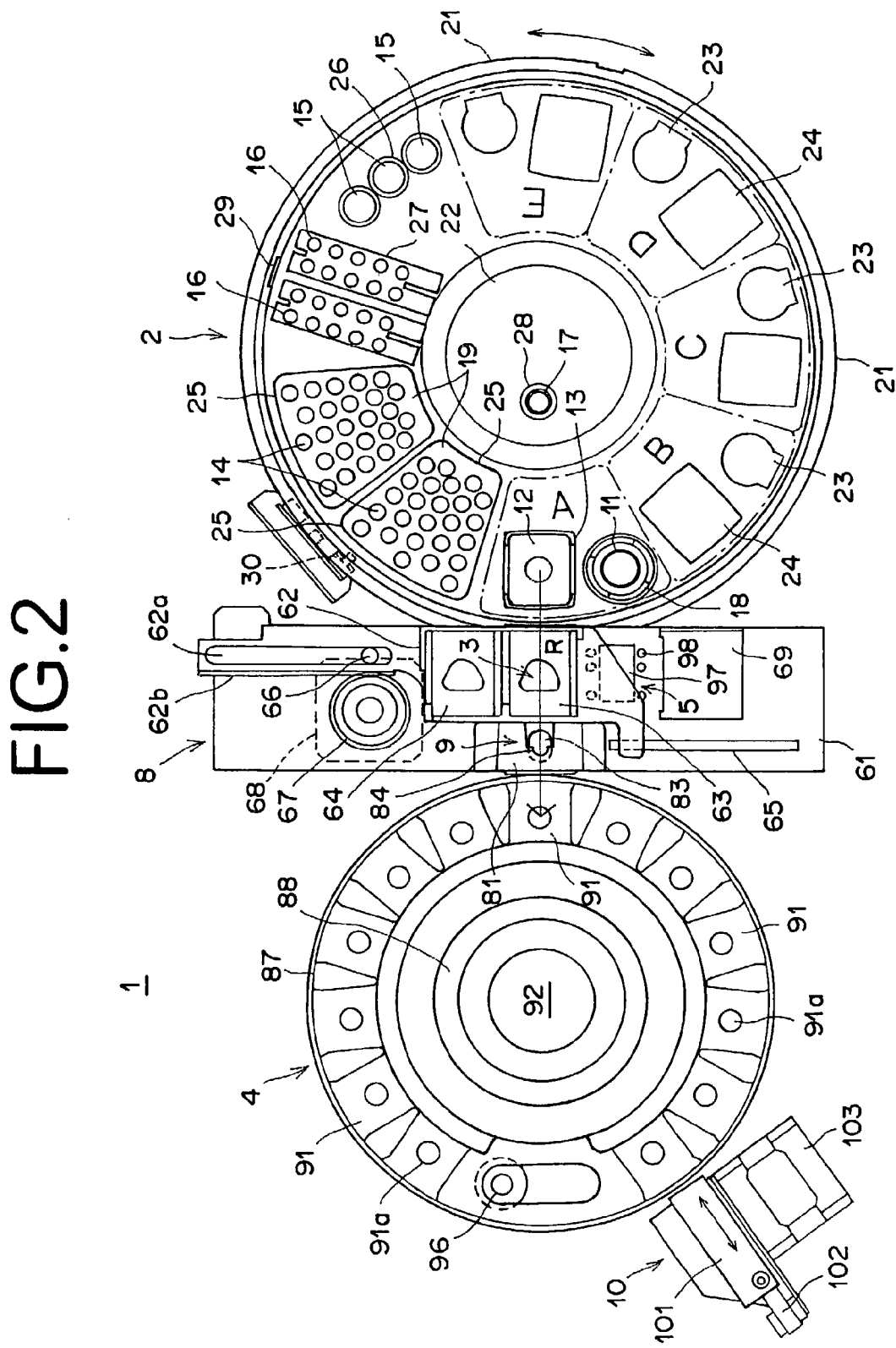
FIG. 2 is a plan view showing a major part of the embodiment of FIG. 1 with a spotting nozzle unit being omitted for clearness.
Figure 3:
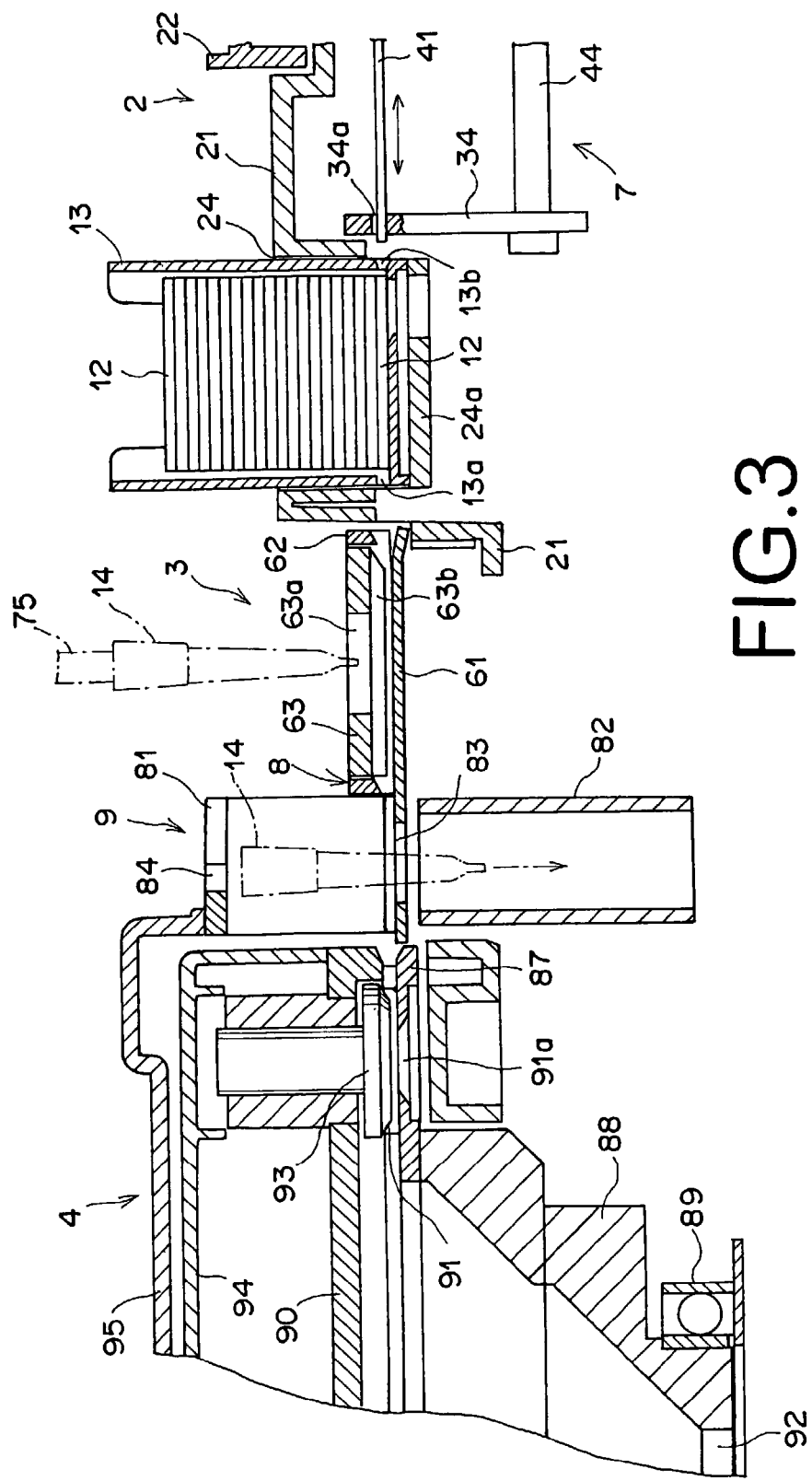
FIG. 3 is a sectional front view showing sections along an element conveyance path for dry chemical analysis elements.
Figure 4:
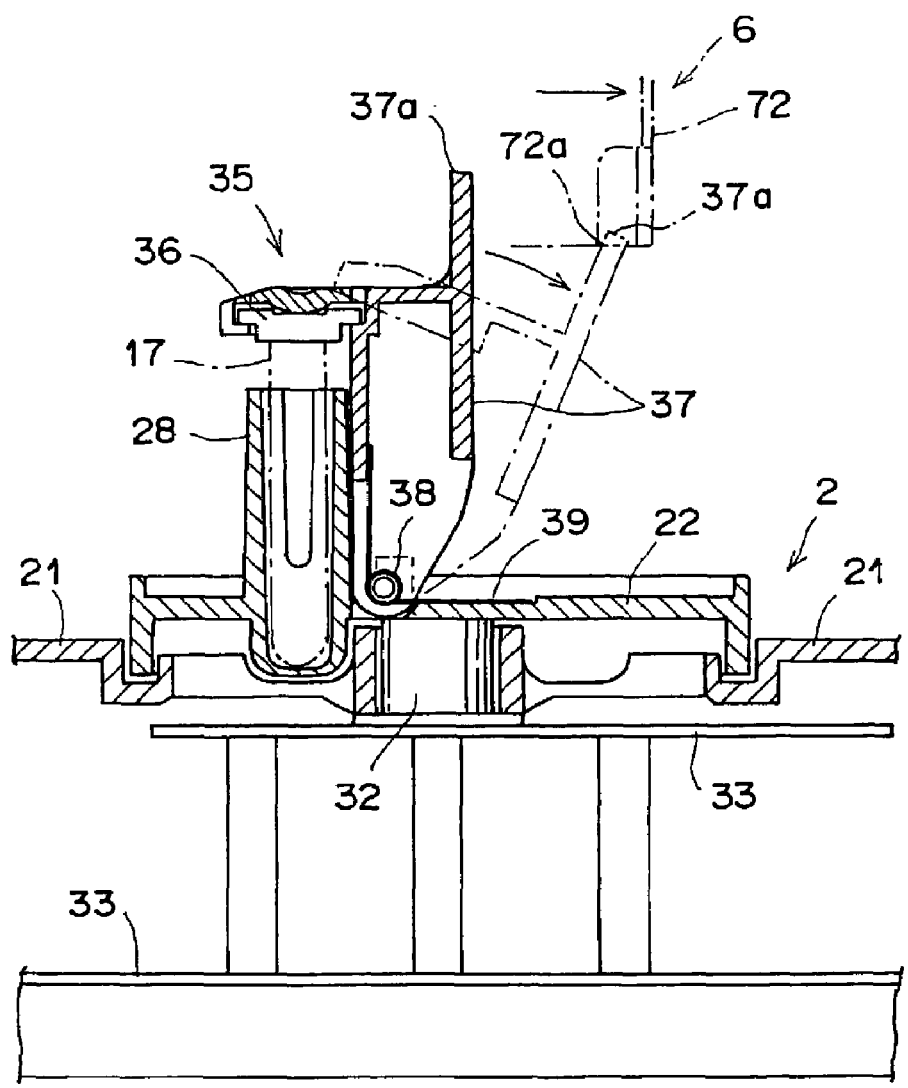
FIG. 4 is a sectional view showing a reference liquid loading section.
Figure 5:
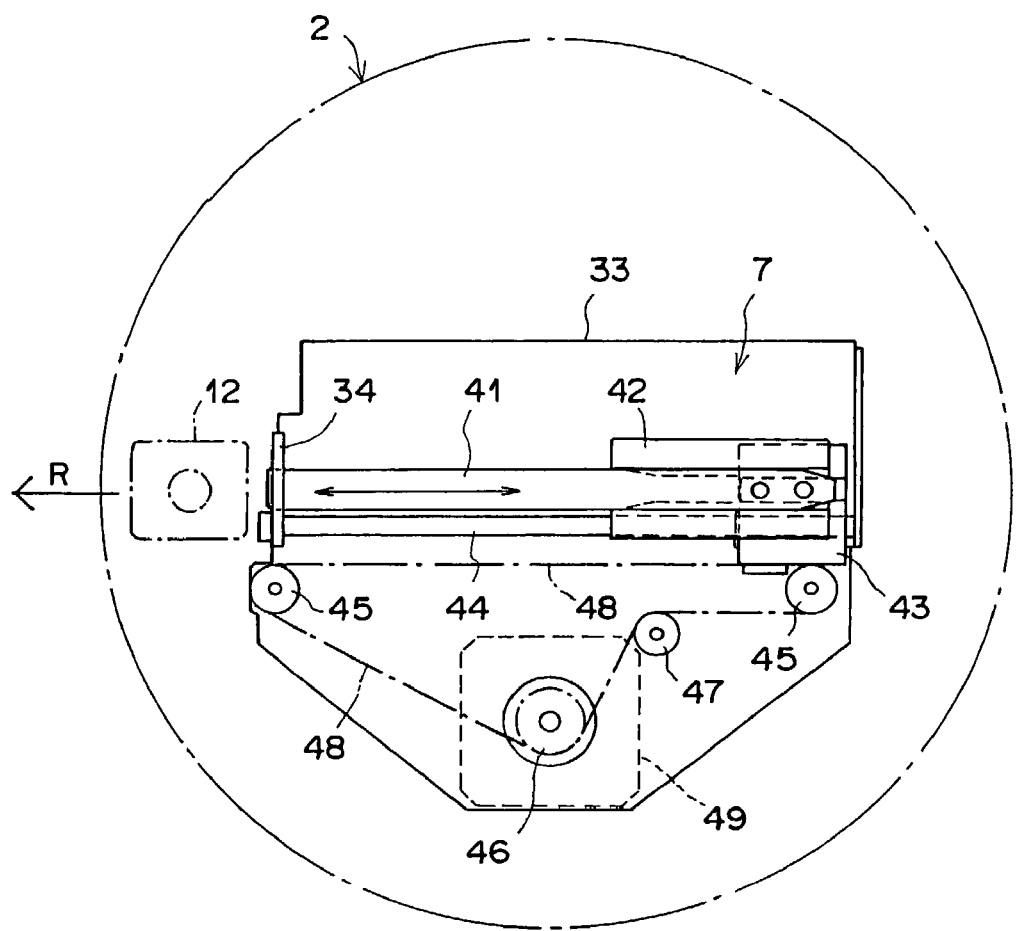
FIG. 5 is a schematic plan view showing an element conveying mechanism.
Figure 6:
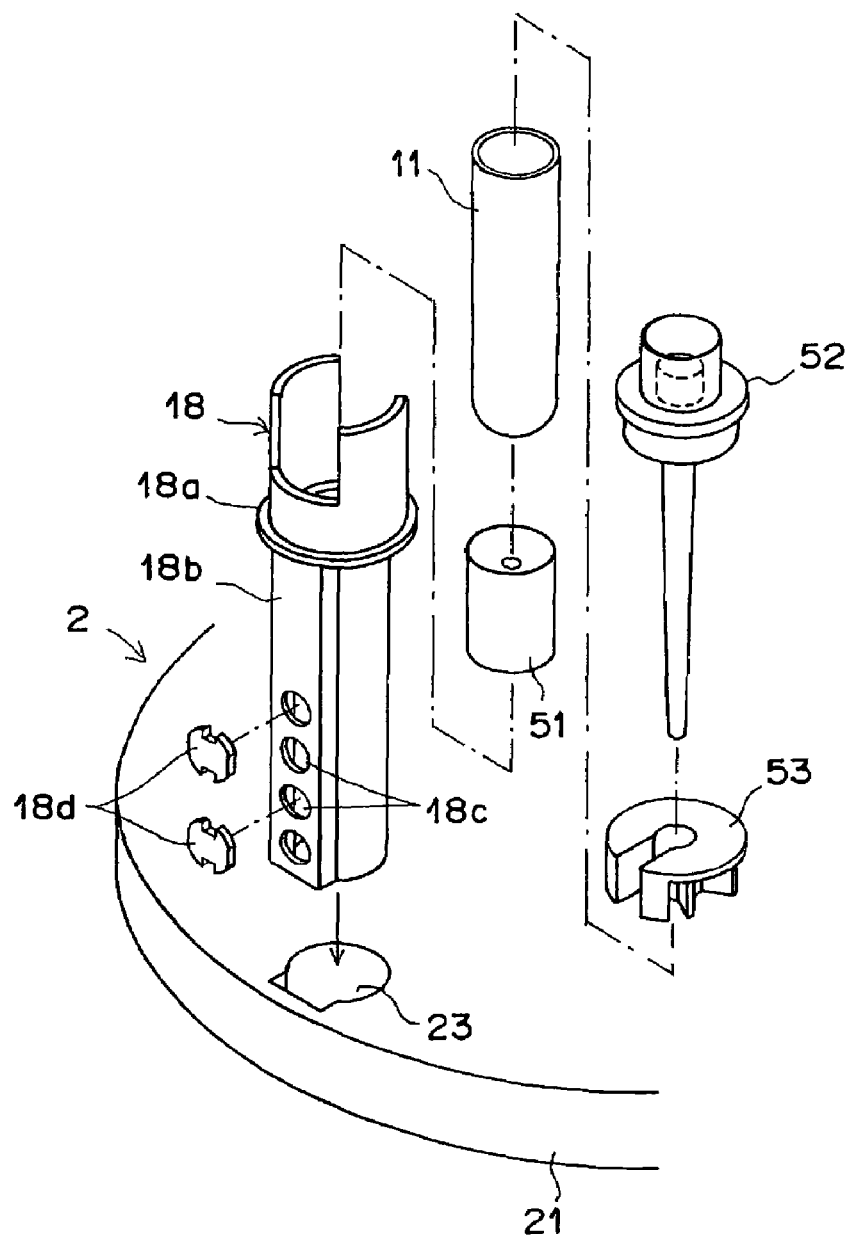
FIG. 6 is an exploded perspective view showing a sample adapter for loading of a sample vessel.

FIG. 1 is a partially sectional front view showing an embodiment of the biochemical analysis apparatus in accordance with the present invention. FIG. 2 is a plan view showing a major part of the embodiment of FIG. 1 with a spotting nozzle unit being omitted for clearness. FIG. 3 is a sectional front view showing sections along an element conveyance path for dry chemical analysis elements. FIG. 4 is a sectional view showing a reference liquid loading section. FIG. 5 is a schematic plan view showing an element conveying mechanism. FIG. 6 is an exploded perspective view showing a sample adapter for loading of a sample vessel.

A biochemical analysis apparatus 1 comprises a sampler tray 2, a spotting section 3, a first incubator 4, a second incubator 5, a spotting nozzle unit 6, an element conveying mechanism 7, a transfer mechanism 8, a tip scrapping section 9, and an element scrapping mechanism 10.

The sampler tray 2 has a circular shape and is loaded with a plurality of sample vessels 11, 11, . . . , each of which accommodates one of samples, a plurality of element cartridges 13, 13, . . . , each of which accommodates a plurality of dry chemical analysis elements 12, 12, . . . (colorimetric-type dry chemical analysis elements and/or electrolyte-type dry chemical analysis elements) having not been used, and expendables (nozzle tips 14, 14, . . . , diluent liquid vessels 15, 15, 15, mixing cups 16, 16, . . . , and a reference liquid vessel 17). As illustrated in FIG. 6, each of the sample vessels 11, 11, . . . is loaded via a sample adapter 18 on the sampler tray 2. The nozzle tips 14, 14, . . . are accommodated in each of tip racks 19, 19 and are loaded in this form on the sampler tray 2.

The spotting section 3 is located on an extension of a center line of the sampler tray 2. In the spotting section 3, a sample, such as blood plasma, whole blood, blood serum, or urine, is spotted to the dry chemical analysis element 12 having been conveyed into the spotting section 3. Specifically, with the spotting nozzle unit 6, the sample is spotted onto the colorimetric-type dry chemical analysis element 12. Also, the sample and a reference liquid are spotted onto the electrolyte-type dry chemical analysis element 12. The tip scrapping section 9 for scrapping each of the nozzle tips 14, 14, . . . is located on the side downstream from the spotting section 3.

The first incubator 4 has a circular shape and is located at a position on an extension of the tip scrapping section 9. The first incubator 4 accommodates the dry chemical analysis elements 12, 12, . . . , which are of the calorimetric types, and keeps the temperature of the colorimetric-type dry chemical analysis elements 12, 12, . . . at a constant temperature for a predetermined length of time in order to perform colorimetry. As illustrated in FIG. 2, the second incubator 5 is located at a position in the vicinity of a side of the spotting section 3. The second incubator 5 accommodates the dry chemical analysis element 12, which is of the electrolyte type. Also, the second incubator 5 keeps the temperature of the electrolyte-type dry chemical analysis element 12 at a constant temperature for a predetermined length of time in order to perform potentiometry.

As illustrated in FIG. 5, the element conveying mechanism 7 is located within the sampler tray 2. The element conveying mechanism 7 conveys the dry chemical analysis elements 12, 12, . . . one after another from the sampler tray 2 into the first incubator 4 along a straight element conveyance path R. As illustrated in FIG. 2, the element conveyance path R connects a center point of the sampler tray 2 and a center point of the first incubator 4 with each other and passes through the spotting section 3 and the tip scrapping section 9. The transfer mechanism 8 is formed so as to act also as the spotting section 3. The transfer mechanism 8 transfers the electrolyte-type dry chemical analysis element 12 from the spotting section 3 into the second incubator 5 along a direction normal to the element conveyance path R.

The spotting nozzle unit 6 is located at an upper part of the biochemical analysis apparatus 1. The spotting nozzle unit 6 is provided with spotting nozzles 75, 75. The spotting nozzles 75, 75 move on the straight line identical with the element conveyance path R described above in order to perform the spotting of the samples and the reference liquid, and dilution of the samples with a diluent liquid. The nozzle tip 14 is fitted to a bottom end of each of the spotting nozzles 75, 75. Each of the spotting nozzles 75, 75 sucks the sample, the reference liquid, or the like, into the nozzle tip 14 and discharges the sucked liquid from the nozzle tip 14. The spotting nozzle unit 6 is provided with syringe means (not shown) for performing the suction and the discharging of the liquid. In the tip scrapping section 9, the nozzle tip 14, which has been used, is removed from each of the spotting nozzles 75, 75, allowed to fall, and thus scrapped.

The element scrapping mechanism 10 is associated with the first incubator 4. The element scrapping mechanism 10 pushes the colorimetric-type dry chemical analysis element 12, which has been used for the analysis, toward a center region of the first incubator 4. At the center region of the first incubator 4, the colorimetric-type dry chemical analysis element 12 is allowed to fall and is thus scrapped. The colorimetric-type dry chemical analysis element 12 is also capable of being scrapped by the element conveying mechanism 7 described above. The electrolyte-type dry chemical analysis element 12, which has been used for the analysis at the second incubator 5, is scrapped by the transfer mechanism 8 described above into a scrapping hole 69.

Though not shown, a blood filtering unit for separating blood plasma from blood is located in the vicinity of the sampler tray 2.

The biochemical analysis apparatus 1 will hereinbelow be described in more detail. The sampler tray 2 comprises a circular rotating disk 21, which is capable of being rotated forwardly and reversely, and a circular disk-shaped non-rotating section 22, which is formed at the center region of the sampler tray 2.

As illustrated in FIG. 2, the rotating disk 21 is provided with five sample loading sections 23, 23, . . . (indicated by A, B, C, D, and E). Each of the sample loading sections 23, 23, . . . supports the sample vessel 11, such as a blood-collecting tube accommodating the sample, via the sample adapter 18. The rotating disk 21 is also provided with five element loading sections 24, 24, . . . , each of which is located in the vicinity of one of the sample loading sections 23, 23, . . . . . Each of the element loading sections 24, 24, . . . supports the element cartridge 13, which accommodates the plurality of the dry chemical analysis elements 12, 12, . . . having not been used. Ordinarily, multiple kinds of dry chemical analysis elements 12, 12, . . . are prepared in accordance with the types of analyses of the samples. The rotating disk 21 is further provided with two tip loading sections 25, 25. Each of the tip loading sections 25, 25 supports a tip rack 19 having a plurality of support holes arrayed for accommodating the plurality of the nozzle tips 14, 14, . . . . The rotating disk 21 is still further provided with a diluent liquid loading section 26 for supporting the three diluent liquid vessels 15, 15, 15, which accommodate the diluent liquid. The rotating disk 21 is also provided with a cup loading section 27 for supporting a plurality of the mixing cups 16, 16, . . . , in each of which the diluent liquid and the sample are to be mixed with each other. (The mixing cups 16, 16, . . . are formed as cup-shaped recesses located on a molded product.) The sample loading sections 23, 23, . . . , the element loading sections 24, 24, . . . , the tip loading sections 25, 25, the diluent liquid loading section 26, and the cup loading section 27 are located around the center region of the rotating disk 21.

The non-rotating section 22 is provided with a cylindrical reference liquid loading section 28 for supporting the reference liquid vessel 17, which accommodates the reference liquid. The reference liquid loading section 28 is located on the extension of the element conveyance path R and within the movement range of the spotting nozzles 75, 75. As illustrated in FIG. 4, an evaporation preventing cover 35, which opens and closes the opening of the reference liquid vessel 17, is located at the reference liquid loading section 28.

The rotating disk 21 described above is supported by three support rollers 31, 31, 31, which are located at an outer peripheral region of the rotating disk 21. As illustrated in FIG. 4, the center region of the rotating disk 21 is supported for rotation around a support shaft 32. Also, a timing belt (not shown) is threaded over the outer periphery of the rotating disk 21. The timing belt is rotated forwardly or reversely by a driving motor. A bottom end of the support shaft 32 is secured to a support frame 33. The center region of the circular non-rotating section 22 is secured to a top end of the support shaft 32.

As illustrated in FIG. 4, the evaporation preventing cover 35 comprises a swinging member 37 provided with a cover member 36, which is to be press-fitted to the opening of the reference liquid vessel 17. A bottom end of the swinging member 37 is pivotably supported on the non-rotating section 22 by a pin 38, such that the swinging member 37 is capable of being swung. Also, the swinging member 37 is urged by a torsion spring 39 toward the direction which closes the opening of the reference liquid vessel 17. Opening and closing operations of the evaporation preventing cover 35 are interlocked with the movement of the spotting nozzle unit 6. Specifically, the swinging member 37 has an engagement region 37a, which is projected at the top end region of the swinging member 37. The engagement region 37a of the swinging member 37 is capable of being brought into abutment with a bottom end corner region 72a of a moving frame 72 of the spotting nozzle unit 6.

Also, when the moving frame 72 of the spotting nozzle unit 6 is moved to the position above the reference liquid loading section 28 in order to perform the suction of the reference liquid with one of the spotting nozzles 75, 75, the bottom end corner region 72a of the moving frame 72 comes into abutment with the engagement region 37a of the evaporation preventing cover 35. As a result, the swinging member 37 is swung to the opening position indicated by the chained line. Also, the cover member 36 is moved upwardly and opens the reference liquid vessel 17. Therefore, it becomes possible for the spotting nozzle 75 to suck the reference liquid accommodated in the reference liquid vessel 17. When the moving frame 72 is moved toward the spotting section 3, the swinging member 37 is swung by the urging force of the torsion spring 39 toward the closing direction, and the cover member 36 closes the opening of the reference liquid vessel 17. In this state, the reference liquid is prevented from evaporating. Therefore, the problems are capable of being prevented from occurring in that the accuracy of analysis becomes low due to a change in concentration of the reference liquid.

The element conveying mechanism 7 is located at the support frame 33 within the sampler tray 2. As illustrated in FIG. 5, the element conveying mechanism 7 is provided with an element conveying member (a conveying bar) 41, which is located along the radial direction of the sampler tray 2. The element conveying member 41 is capable of sliding toward the center position of the first incubator 4. The distance of conveyance with the element conveying mechanism 7 is set such that a leading end of the element conveying member 41 pushes each dry chemical analysis element 12 out of the element cartridge 13 supported by the element loading section 24 through control of the forward movement of the element conveying member 41, conveys the dry chemical analysis element 12 into the spotting section 3, and conveys the spotted dry chemical analysis element 12 into the first incubator 4.

Also, as illustrated in FIG. 2, besides the element loading sections 24, 24, . . . , the rotating disk 21 of the sampler tray 2 is provided with an insertion hole 29 acting as a path for the element conveying member 41. The insertion hole 29 may be located, for example, at a position under the cup loading section 27. When necessary, e.g. when clogging of the dry chemical analysis element 12, or the like, occurs, the insertion hole 29 allows the element conveying member 41 to perform the forward movement accompanying no element conveyance.

A slider 43 is secured to a bottom surface of a tail end of the element conveying member 41. The slider 43 is supported for sliding movement by a guide rod 44, which is secured to the support frame 33 and extends in parallel with the element conveyance path R. Also, a certain region of a belt 48 is secured to the slider 43. The belt 48 is threaded over guide pulleys 45, 45, which are located on two sides of the support frame 33, a driving pulley 46, which is rotated by a conveyor motor 49, and a tension pulley 47. The driving pulley 46 is rotated by the conveyor motor 49 in order to move the slider 43, and the element conveying member 41 is thereby moved forwardly or backwardly. When the element conveying member 41 is moved backwardly, the position of the tail end of the element conveying member 41 is adjusted by a guide member 42. As illustrated in FIG. 3, the leading end of the element conveying member 41 is inserted through a guide hole 34a of a vertical plate 34. The element conveying member 41 slides in the guide hole 34a.

As illustrated in FIG. 3, the element cartridge 13 has a box-like shape and is open at a top region and side regions. The dry chemical analysis elements 12, 12, . . . having not been used are introduced into the element cartridge 13 from above. Ordinarily, the plurality of the dry chemical analysis elements 12, 12, . . . , which may be of different types, are superposed one upon another in the element cartridge 13. The element cartridge 13, which has been fitted into one of the element loading sections 24, 24, . . . of the sampler tray 2, is supported by a bottom wall 24a of the element loading section 24. The lowest dry chemical analysis element 12, which is among the plurality of the dry chemical analysis elements 12, 12, . . . superposed one upon another in the element cartridge 13, is located at a height identical with the height of the plane of conveyance of the dry chemical analysis element 12. A left side wall of the element cartridge 13 in FIG. 3 is provided with an opening 13a at a position corresponding to the lowest dry chemical analysis element 12, which is among the plurality of the dry chemical analysis elements 12, 12, . . . superposed one upon another in the element cartridge 13. The size of the opening 13a of the element cartridge 13 is set such that only one dry chemical analysis element 12 is capable of passing through the opening 13a. A right side wall of the element cartridge 13 in FIG. 3 is provided with an opening 13b, through which the element conveying member 41 is capable of passing.

As illustrated in FIG. 6, the sample adapter 18, which is used for loading the sample vessel 11 onto the sampler tray 2, has a cylindrical shape. The sample vessel 11 is inserted into the sample adapter 18 from above. The sample adapter 18 is provided with a flange 18a around the outer periphery of the sample adapter 18. When the sample adapter 18 is inserted into a hole of one of the sample loading sections 23, 23, . . . of the sampler tray 2, the flange 18a of the sample adapter 18 comes into abutment with the top surface of the rotating disk 21, and the sample adapter 18 is thus supported by the rotating disk 21. Also, the sample adapter 18 is provided with a convex region 18b, which is protruded from a front surface of the cylinder under the flange section 18a. The convex region 18b of the sample adapter 18 acts to determine the orientation of the sample adapter 18 when the sample adapter 18 is inserted into the hole of the sample loading section 23 of the sampler tray 2. Further, an identification region 18c comprising four holes is formed in the front surface of a lower area of the convex region 18b. In accordance with the kind of the sample (processing information), the kind (the size) of the sample vessel 11, and the like, identification pins 18d, 18d are selectively fitted into the holes of the identification region 18c. At an initial stage of the analysis, the identification information represented by the identification pins 18d, 18d is read with an identification sensor 30 (shown in FIG. 2), which is located at the outer periphery of the sampler tray 2. In this manner, a judgment is made as to whether the sample is to be or is not to be diluted, whether blood filtration is to be or is not to be performed, and the like. Also, an amount of change in liquid level due to the size of the sample vessel 11 is calculated, and processing control is made in accordance with the calculated amount of change in liquid level.

A height adjusting member 51 is inserted into the bottom area in the sample adapter 18, and the bottom height in the sample adapter 18 is thus capable of being adjusted in accordance with the length of the sample vessel 11. In cases where the blood filtration is to be performed, after the sample vessel 11 has been inserted into the sample adapter 18, a holder 52 provided with a filter is fitted into the sample vessel 11 via a spacer 53.

The sample vessel 11 described above is capable of being fitted arbitrarily into one of the sample loading sections 23, 23, . . . (A through E) of the rotating disk 21. Also, the element cartridge 13 described above is capable of being fitted arbitrarily into one of the element loading sections 24, 24, . . . (A through E) of the rotating disk 21. Further, before the analysis is made, the sample vessel 11 is capable of being changed for a different sample vessel 11, and the element cartridge 13 is capable of being changed for a different element cartridge 13. Therefore, in cases where an interrupting sample analysis is to be performed urgently, the analysis of the sample is capable of being conducted immediately.

The dry chemical analysis element 12, which is to be introduced into the element cartridge 13, will be described hereinbelow in detail. The colorimetric-type dry chemical analysis element 12, which is used for the analysis of the degree of coloration of the sample, comprises a rectangular mount and a reagent layer, which is located within the mount. A spotting hole is formed at a center region of the mount, and the sample is spotted onto the spotting hole of the mount. The electrolyte-type dry chemical analysis element 12, which is used for the analysis of the ionic activity of the specific ion contained in the sample, is provided with two liquid feeding holes. The sample is spotted onto one of the two liquid feeding holes, and the reference liquid, whose ionic activity is known, is spotted onto the other liquid feeding hole. The electrolyte-type dry chemical analysis element is also provided with three ion selective electrode pairs, which are to be electrically connected to potential difference measuring probes of potential difference measuring means for the analysis of the ionic activity of the specific ion. A bar code (not shown) representing information for specifying the type of the analysis, or the like, is attached to the back surface of each of the colorimetric-type dry chemical analysis element 12 and the electrolyte-type dry chemical analysis element 12.

As illustrated in FIG. 2 and FIG. 3, the spotting section 3 and the transfer mechanism 8 comprise a common support base 61, which is long in the direction normal to the element conveyance path R. The support base 61 is located between the sampler tray 2 and the first incubator 4. Also, a sliding frame 62 is located on the plunger 61, such that the sliding frame 62 is capable of moving. A main element retainer 63 and a subsidiary element retainer 64 are fitted to the sliding frame 62. The main element retainer 63 and the subsidiary element retainer 64 are located at positions adjacent to each other and are capable of moving together. As illustrated in FIG. 3, the main element retainer 63 is provided with a spotting opening 63a. Also, as illustrated in FIG. 3, the bottom surface of the main element retainer 63, which bottom surface stands facing the support base 61, is provided with a recess 63b, through which the dry chemical analysis element 12 is capable of being conveyed along the element conveyance path R. The dry chemical analysis element 12 is moved so as to slide on the support base 61. The subsidiary element retainer 64 is constituted in the same manner as that in the main element retainer 63. One end region of the sliding frame 62 is guided by a guide bar 65. The other end region of the sliding frame 62 is provided with a long groove 62a. The long groove 62a of the sliding frame 62 is engaged with a pin 66, and the sliding frame 62 is capable of moving in the direction normal to the element conveyance path R. The sliding frame 62 is also provided with a rack gear 62b. The rack gear 62b of the sliding frame 62 is engaged with a driving gear 67. The driving gear 67 is rotated by a driving motor 68 in order to move the sliding frame 62.

The support base 61 is provided with the second incubator 5 described above. The second incubator 5 is located at a position along the side of the spotting section 3 (i.e., along the side of the spotting position). Specifically, the second incubator 5 is located at the position on the side downstream from the spotting section 3 with respect to the direction of movement of the sliding frame 62. Also, the scrapping hole 69 described above is formed along the side of the second incubator 5 and at a position on the side downstream from the second incubator 5 with respect to the direction of movement of the sliding frame 62.

In the ordinary state illustrated in FIG. 2, the sliding frame 62 is kept stationary at the position such that the main element retainer 63 is located at the position corresponding to the position of the spotting section 3. In this state, the spotting onto the dry chemical analysis element 12, which has been conveyed from the sampler tray 2 into the spotting section 3, is performed. In cases where the spotting onto the colorimetric-type dry chemical analysis element 12 has been performed, the colorimetric-type dry chemical analysis element 12, which has been spotted, is pushed by the element conveying member 41 out of the spotting section 3 and transferred into the first incubator 4. In cases where the spotting onto the electrolyte-type dry chemical analysis element 12 has been performed, the sliding frame 62 is moved, and the electrolyte-type dry chemical analysis element 12, which has been spotted, is slid on the support base 61 in the state, in which the electrolyte-type dry chemical analysis element 12 is being supported by the main element retainer 63. In this manner, the electrolyte-type dry chemical analysis element 12 is transferred into the second incubator 5. At the second incubator 5, the potential difference measurement is performed. At this time, the subsidiary element retainer 64 of the sliding frame 62 moves to the spotting section 3 (i.e., the spotting position). Therefore, with respect to the colorimetric-type dry chemical analysis element 12, which may be conveyed thereafter from the sampler tray 2 into the spotting section 3, the sample spotting and the conveyance into the first incubator 4 are capable of being performed. When the analysis at the second incubator 5 is finished, the sliding frame 62 is moved even further in order to transfer the electrolyte-type dry chemical analysis element 12, which has been analyzed, into the scrapping hole 69. The electrolyte-type dry chemical analysis element 12, which has been analyzed, is thus allowed to fall and scrapped.

As illustrated in FIG. 1, the spotting nozzle unit 6 comprises the moving frame 72. The moving frame 72 is supported on a horizontal guide rail 71 of a secured frame 70, such that the moving frame 72 is capable of being moved horizontally. The horizontal guide rail 71 extends in parallel with the element conveyance path R. A vertical guide rail 73 is located at the center region of the moving frame 72. Also, two nozzle securing bases 74, 74 are supported for vertical movement on opposite sides of the vertical guide rail 73. A top end of the rod-shaped spotting nozzle 75, which extends vertically, is secured to each of the two nozzle securing bases 74, 74.

An upwardly extending connection shaft 76 is secured to each of the nozzle securing bases 74, 74. The top end region of each of the connection shafts 76, 76 is inserted into one of driving force transmitting members 77, 77. Also, a compression spring 80 is located in a compressed state around the outer periphery of the region of each of the connection shafts 76, 76, which region is disposed between the nozzle securing base 74 and the driving force transmitting member 77. Therefore, each of the nozzle securing bases 74, 74 is capable of moving vertically together with the corresponding driving force transmitting member 77. Also, in cases where the nozzle tip 14 is to be fitted onto the bottom end region of the spotting nozzle 75, the driving force transmitting member 77 is capable of compressing the compression spring 80 and moving downwardly with respect to the nozzle securing base 74 in order to yield the force for fitting the nozzle tip 14.

Each of belts 79, 79 is threaded over upper and lower pulleys 78, 78. Each of the driving force transmitting members 77, 77 described above is secured to one of the belts 79, 79. Each of the belts 79, 79 is moved by a motor (not shown), and each of the driving force transmitting members 77, 77 is thereby moved vertically. A balancing weight 99 is secured to an outer region of each of the belts 79, 79 in order to prevent the spotting nozzle 75 from moving down when each of the belts 79, 79 is not driven.

The moving frame 72 is moved horizontally by a belt driving mechanism (not shown). The horizontal movements and the vertical movements of the two nozzle securing bases 74, 74 are controlled such that each of the two nozzle securing bases 74, 74 independently undergoes the vertical movement. The two spotting nozzles 75, 75 move together in the horizontal direction on a straight line identical with the straight line of the element conveyance path R. Also, each of the two spotting nozzles 75, 75 independently undergoes the vertical movement. By way of example, one of the two spotting nozzles 75, 75 is used for the sample, and the other spotting nozzle 75 is used for the diluent liquid and the reference liquid.

Each of the spotting nozzles 75, 75 has a rod-like shape. An axially extending air path is formed within each of the spotting nozzles 75, 75. The pipette-shaped nozzle tip 14 is fitted in a sealed state onto the bottom end region of each of the spotting nozzles 75, 75. An air tube, which is connected to a syringe pump (not shown), or the like, is connected to each of the spotting nozzles 75, 75 in order to supply the suction pressure and the discharging pressure to each of the spotting nozzles 75, 75. The nozzle tip 14, which has been used, is removed from the bottom end region of the spotting nozzle 75 in the tip scrapping section 9. The nozzle tip 14 removed from the bottom end region of the spotting nozzle 75 is allowed to fall and scrapped.

The tip scrapping section 9 is located at the position on the element conveyance path R and on the side downstream from the spotting section 3 with respect to the direction of conveyance of the dry chemical analysis element 12 along the element conveyance path R. The tip scrapping section 9 vertically intersects with the plane of conveyance of the dry chemical analysis element 12. The tip scrapping section 9 comprises an upper member 81 and a lower member 82. The region of the support base 61 described above, which region is located at the position corresponding to the position of the tip scrapping section 9, is provided with an elliptic fall opening 83. The upper member 81 of the tip scrapping section 9 is secured to the top surface of the support base 61. Also, the upper member 81 of the tip scrapping section 9 is provided with an engagement cut-away region 84 at a position exactly above the fall opening 83 of the support base 61. The lower member 82 of the tip scrapping section 9 is formed in a cylindrical shape and is located under the bottom surface of the support base 61 so as to surround the region beneath the fall opening 83 of the support base 61. The lower member 82 of the tip scrapping section 9 guides the nozzle tip 14, which falls from the region within the upper member 81 of the tip scrapping section 9 through the fall opening 83 of the support base 61.

In cases where the nozzle tip 14 having been fitted onto the spotting nozzle 75 is to be removed from the spotting nozzle 75 and scrapped, the spotting nozzle 75, onto which the nozzle tip 14 has been fitted, is moved downwardly into the region within the upper member 81 of the tip scrapping section 9 and is then moved toward the left side in FIG. 3 until the top end region of the nozzle tip 14 engages with the engagement cut-away region 84 of the upper member 81 of the tip scrapping section 9. Thereafter, the spotting nozzle 75 is moved upwardly, and the nozzle tip 14 is thereby removed from the spotting nozzle 75. The nozzle tip 14 having thus been removed from the spotting nozzle 75 is allowed to fall from the region within the upper member 81 of the tip scrapping section 9 through the fall opening 83 of the support base 61 into the lower member 82 of the tip scrapping section 9. The nozzle tip 14 is thus scrapped.

As illustrated in FIG. 1, FIG. 2, and FIG. 3, the first incubator 4 for performing the colorimetry comprises an annular rotating member 87, which is located at an outer peripheral region of the first incubator 4. A tapered rotating cylinder 88 is secured to a bottom surface of an inner peripheral region of the rotating member 87. The tapered rotating cylinder 88 is supported for rotation by a bearing 89, which is located at a bottom area of the tapered rotating cylinder 88. A top member 90 is located on the rotating member 87, such that the top member 90 is capable of rotating together with the rotating member 87. The top member 90 has a flat bottom surface. A plurality of recesses (in the case of FIG. 1, 13 recesses) are formed at predetermined intervals in the top circumferential surface of the rotating member 87. In this manner, element compartments 91, 91, . . . are formed as slit-shaped spaces between the rotating member 87 and the top member 90. The height of the bottom surface of each of the element compartments 91, 91, . . . coincides with the height of the plane of conveyance of the dry chemical analysis element 12. The inner hole of the tapered rotating cylinder 88 acts as a scrapping hole 92 for the dry chemical analysis element 12 having been used for the analysis. The area of each of the element compartments 91, 91, . . . , which area stands facing the center region of the first incubator 4, communicates with the scrapping hole 92. The dry chemical analysis element 12, which has been accommodated in each of the element compartments 91, 91, . . . and has been used for the analysis, is moved from the element compartment 91 toward the center region of the first incubator 4. The dry chemical analysis element 12 is thus allowed to fall through the scrapping hole 92 and scrapped.

The top member 90 is provided with heating means (not shown). The temperature of the dry chemical analysis element 12, which has been accommodated in each of the element compartments 91, 91, . . . , is kept at a predetermined temperature by the temperature adjustment with the heating means. The top member 90 is also provided with retaining members 93, 93, . . . at the positions corresponding to the element compartments 91, 91, . . . . Each of the retaining members 93, 93, . . . retains the mount of the dry chemical analysis element 12 from above in order to prevent the sample from evaporating. A heat insulating cover 94 is located so as to cover the top surface of the top member 90. Also, the entire area of the first incubator 4 is covered with a light blocking cover 95.

Further, an opening 91a for photometry is formed at a center area of the bottom surface of each of the element compartments 91, 91, . . . of the rotating member 87, which element compartments 91, 91, . . . accommodate the dry chemical analysis elements 12, 12, . . . . Through the opening 91a of each of the element compartments 91, 91, ..., the measurement of a reflection optical density of each dry chemical analysis element 12 is performed with a photometric head 96, which is located at the position shown in FIG. 2. A density reference plate (not shown) is located at a certain area of the rotating member 87.

In order for the first incubator 4 to be rotated, a timing belt (not shown) is threaded over the outer peripheral region of the tapered rotating cylinder 88, which supports the rotating member 87. The timing belt is also threaded over a driving pulley (not shown) of a driving motor (not shown). The rotating member 87 is reciprocally rotated by the forward and reverse rotations of the driving motor. The first incubator 4 is reciprocally rotated by angles falling within predetermined angle ranges, such that the operations described below are performed. Specifically, firstly, the optical densities of the white-black density reference plate are detected with the photometric head 96, which is located under a predetermined position of rotation of the first incubator 4, and calibration is conducted. Thereafter, the optical densities of the dry chemical analysis elements 12, 12, ... having been inserted respectively into the element compartments 91, 91, ..., which optical densities depend on the coloration reactions occurring with the dry chemical analysis elements 12, 12, ..., are measured successively. After the series of the measurements are performed, the first incubator 4 is rotated reversely to a reference position. Thereafter, the subsequent measurements are performed.

As illustrated in FIG. 2, the element scrapping mechanism 10, which is associated with the first incubator 4, comprises a scrapping bar 101. The scrapping bar 101 is capable of being moved from the outer peripheral side of the first incubator 4 toward the center region of the first incubator 4 and thus entered into each of the element compartments 91, 91, .... Also, the scrapping bar 101 is capable of being moved reversely and retracted from the element compartment 91. A tail end region of the scrapping bar 101 is secured to a belt 102, which is moved horizontally by a driving motor 103. The scrapping bar 101 moves in accordance with the movement of the belt 102 in order to push the dry chemical analysis element 12, which has been used for the analysis, out of the element compartment 91 into the scrapping hole 92. A collecting box (not shown) for collecting the dry chemical analysis elements 12, 12, ..., which have been used for the analyses, is located under the scrapping hole 92.

In the second incubator 5 for the measurement of the ionic activity of the specific ion, the main element retainer 63 of the sliding frame 62 described above acts as a top member, and a single element compartment is formed by the recess 63b of the main element retainer 63 and on a top surface of a measuring main body 97. The second incubator 5 is provided with heating means (not shown). The temperature of an ionic activity measurement region of the dry chemical analysis element 12, which has been accommodated in the element compartment, is kept at a predetermined temperature by the temperature adjustment with the heating means. Also, three pairs of potential difference measuring probes 98, 98, ... for the measurement of the ionic activity are located along the sides of the measuring main body 97. The three pairs of the potential difference measuring probes 98, 98, ... are capable of being moved and brought into contact with the ion selective electrodes of the dry chemical analysis element 12. After the sample has been spotted onto one of the two liquid feeding holes of the dry chemical analysis element 12, and the reference liquid, whose ionic activity is known, has been spotted onto the other liquid feeding hole of the dry chemical analysis element 12, the potential difference, which corresponds to the difference between the ionic activity of a specific ion contained in the sample and the ionic activity of the specific ion contained in the reference liquid, occurs between each pair of the ion selective electrodes. Therefore, in cases where the potential difference occurring between each pair of the ion selective electrodes is measured with one of the three pairs of the potential difference measuring probes 98, 98, ..., the ionic activity of the specific ion contained in the sample is capable of being measured.

As described above, the blood filtering unit (not shown) for separating blood plasma from blood is located in the vicinity of the sampler tray 2. The blood filtering unit operates in the manner described below. Specifically, blood plasma is separated with suction from blood via the holder 52 described above, which has been inserted into the sample vessel (blood-collecting tube) 11 supported by the sampler tray 2 and is provided with the glass fiber filter fitted to the top end opening of the sample vessel 11. Also, the blood plasma, which has been separated from the blood by the filtration, is retained in a cup region located at the top end of the holder 52.

How the biochemical analysis apparatus 1 operates will be described hereinbelow. Firstly, before the analyses are performed, preparation for the analyses is made. Specifically, each of the sample vessels 11, 11, ... accommodating the samples is fitted via the sample adapter 18, whose identification region 18c has been set, into one of the sample loading sections 23, 23, ... of the sampler tray 2. Also, each of the element cartridges 13, 13, ... accommodating the dry chemical analysis elements 12, 12, ... of the kinds corresponding to the types of the analyses of the samples is fitted into one of the element loading sections 24, 24, ..., the one element loading section 24 being located at the position corresponding to the sample vessel 11 to be subjected to the analysis. Further, the tip racks 19, 19 accommodating the nozzle tips 14, 14, ... acting as the expendables, are fitted into the tip loading sections 25, 25. Furthermore, the mixing cups 16, 16, ... are fitted into the cup loading section 27, the diluent liquid vessels 15, 15, 15 are fitted into the diluent liquid loading section 26, and the reference liquid vessel 17 is fitted into the reference liquid loading section 28.

Thereafter, analysis processing is begun. At the initial stage, the rotating disk 21 of the sampler tray 2 is rotated one turn, and the setting of the identification region 18c of the sample adapter 18 is read out by the identification sensor 30. In this manner, with respect to each of the samples having been loaded on the sampler tray 2, a judgment is made as to whether the sample is to be or is not to be diluted, whether blood filtration is to be or is not to be performed, and the like.

In cases where it has been judged that the blood filtration is to be performed with respect to the sample, the whole blood accommodated in the sample vessel 11 is subjected to the filtration with the blood filtering unit, and the blood plasma constituent is obtained. Thereafter, the rotating disk 21 is rotated, and the element cartridge 13 (the element loading section 24) corresponding to the sample to be analyzed is located at the position corresponding to the position of the spotting section 3. A dry chemical analysis element 12 is then conveyed by the element conveying member 41 from the element cartridge 13 into the spotting section 3. At an intermediate point during the conveyance of the dry chemical analysis element 12 from the element cartridge 13 into the spotting section 3, the bar code attached to the dry chemical analysis element 12 is read out. In this manner, the type of the analysis with the dry chemical analysis element 12, or the like, is detected. In cases where it has been detected that the type of the analysis with the dry chemical analysis element 12 is the measurement of the ionic activity, different processing is performed in accordance with the cases of a dilution request type, or the like.

In cases where it has been detected that the type of the analysis with the dry chemical analysis element 12 is the colorimetry, the sampler tray 2 is rotated, and a nozzle tip 14 is located at the position under one of the spotting nozzles 75, 75. The nozzle tip 14 is then fitted onto the spotting nozzle 75. Thereafter, the sampler tray 2 is rotated in order to locate the sample vessel 11 at the position under the spotting nozzle 75, onto which the nozzle tip 14 has been fitted. The spotting nozzle 75 is then moved downwardly, and the sample is sucked from the sample vessel 11 into the nozzle tip 14. Thereafter, the spotting nozzle 75 is moved to the position above the spotting section 3, and the sample is spotted from the nozzle tip 14 onto the dry chemical analysis element 12, which has been conveyed to the spotting section 3.

Thereafter, the colorimetric-type dry chemical analysis element 12, which has been spotted with the sample, is inserted from the spotting section 3 into an element compartment 91 of the first incubator 4. The rotating member 87 of the first incubator 4 is then rotated, and the dry chemical analysis element 12 having been inserted into the element compartment 91 of the first incubator 4 is located at the position which stands facing the photometric head 96. In this state, the reflection optical density of the dry chemical analysis element 12 is measured with the photometric head 96. After the measurement of the reflection optical density of the dry chemical analysis element 12 is finished, the dry chemical analysis element 12 having been measured is pushed out from the element compartment 91 toward the center region of the first incubator 4 and into the scrapping hole 92 and is thus scrapped. Also, the results of the measurement are outputted. Further, the nozzle tip 14 having been used is removed from the spotting nozzle 75 in the tip scrapping section 9. In the tip scrapping section 9, the nozzle tip 14 having been removed from the spotting nozzle 75 is allowed to fall and scrapped. At this stage, the processing of the colorimetry is finished.

In cases where it has been detected that the type of the analysis with the dry chemical analysis element 12 is the dilution request type, e.g. in cases where the concentration of the blood is high and it is regarded that an accurate analysis cannot be made, the sampler tray 2 is rotated, and a nozzle tip 14 is located at the position under one of the spotting nozzles 75, 75 and is then fitted onto the spotting nozzle 75. Thereafter, the sampler tray 2 is rotated in order to locate the sample vessel 11 at the position under the spotting nozzle 75, onto which the nozzle tip 14 has been fitted. The spotting nozzle 75 is then moved downwardly, and the sample is sucked from the sample vessel 11 into the nozzle tip 14. Thereafter, the sampler tray 2 is rotated in order to locate a mixing cup 16 at the position under the spotting nozzle 75, and the sucked sample is introduced from the nozzle tip 14 into the mixing cup 16. The nozzle tip 14 having thus been used is then removed from the spotting nozzle 75. Thereafter, a new nozzle tip 14 is fitted onto the spotting nozzle 75, and the diluent liquid is sucked from a diluent liquid vessel 15 into the new nozzle tip 14. The sucked diluent liquid is then discharged from the nozzle tip 14 into the mixing cup 16, into which the sample has been introduced. Also, the nozzle tip 14 is inserted into the mixing cup 16, and the mixture of the sample and the diluent liquid is stirred through repeated suction of the mixture into the nozzle tip 14 and discharging of the mixture from the nozzle tip 14. The sample having thus been diluted with the diluent liquid is then sucked into the nozzle tip 14. The spotting nozzle 75 fitted with the nozzle tip 14 is then moved to the position above the spotting section 3, and the diluted sample is spotted onto the dry chemical analysis element 12. Thereafter, the photometry, the element scrapping, the outputting of results of the measurement, and the tip scrapping are performed in the same manner as that described above, and the processing is finished.

In cases where it has been detected that the type of the analysis with the dry chemical analysis element 12 is the measurement of the ionic activity, the processing is performed in the manner described below. In the cases of the measurement of the ionic activity, the electrolyte-type dry chemical analysis element 12 is conveyed from the element cartridge 13 into the spotting section 3. Firstly, a nozzle tip 14 is fitted onto one of the spotting nozzles 75, 75, and a sample is sucked from the sample vessel 11 into the nozzle tip 14. Thereafter, a nozzle tip 14 is fitted onto the other spotting nozzle 75, and the reference liquid is sucked from the reference liquid vessel 17 into the nozzle tip 14, which has been fitted onto the other spotting nozzle 75. Thereafter, the sample is spotted from the nozzle tip 14, which has been fitted onto the one spotting nozzle 75, into one of the two liquid feeding holes of the dry chemical analysis element 12. Also, the reference liquid is spotted from the nozzle tip 14, which has been fitted onto the other spotting nozzle 75, into the other liquid feeding hole of the dry chemical analysis element 12.

The dry chemical analysis element 12, which has been spotted with the sample and the reference liquid in the manner described above, is transferred from the spotting section 3 into the second incubator 5 in accordance with the movement of the sliding frame 62. When the dry chemical analysis element 12 has thus been inserted into the second incubator 5, the measurement of the ionic activity of the specific ion contained in the sample is performed with the potential difference measuring probes 98, 98, . . . After the measurement of the ionic activity of the specific ion is finished, the dry chemical analysis element 12 having been measured is transferred into the scrapping hole 69 and scrapped in accordance with the movement of the sliding frame 62. Also, the results of the measurement are outputted. Further, the two nozzle tips 14, 14 having been used are removed from the spotting nozzles 75, 75 and scrapped. At this stage, the processing of the measurement of the ionic activity is finished.

In this embodiment, the dry chemical analysis elements 12, 12, . . . are accommodated in each of the element cartridges 13,13, . . . , and the element cartridges 13, 13, . . . accommodating the dry chemical analysis elements 12, 12, . . . are loaded on the rotating disk 21. However, the dry chemical analysis elements 12, 12, . . . need not necessarily be accommodated in the element cartridges 13, 13, . . . and may be directly loaded on the rotating disk 21.

With the embodiment described above, the plurality of the sample vessels 11, 11, . . . , each of which accommodates one of the samples, the plurality of the element cartridges 13, 13, . . . , each of which accommodates the plurality of the dry chemical analysis elements 12, 12, . . . for the analyses, and the expendables (the nozzle tips 14, 14, . . . , the diluent liquid vessels 15, 15, 15, and the mixing cups 16, 16, . . . ) are loaded on the rotating disk 21 of the sampler tray 2. Also, the reference liquid vessel 17 is loaded on the non-rotating section 22 of the sampler tray 2. Therefore, each of the multiple kinds of the samples is capable of being loaded on the sampler tray 2 as a set together with the necessary dry chemical analysis elements 12, 12, . . . . Accordingly, the loading operation is capable of being performed accurately and easily. Also, a sample to be analyzed urgently is capable of being processed appropriately. Further, the work of the operator is capable of being kept easy, and the analysis processing is capable of being performed efficiently with the small-sized biochemical analysis apparatus.

Also, with the embodiment described above, each of the dry chemical analysis elements 12, 12, . . . is conveyed by the element conveying member 41 from each of the element cartridges 13, 13, . . . , which have been loaded on the sampler tray 2, into the spotting section 3 in the straight line along the element conveyance path R. Also, with the two spotting nozzles 75, 75, which move along the path on the straight line identical with the element conveyance path R, the sample is sucked from the sample vessel 11 loaded on the sampler tray 2, and the reference liquid is sucked from the reference liquid vessel 17 loaded on the sampler tray 2. At the spotting section 3, the spotting of the sample onto the dry chemical analysis element 12 and the spotting of the reference liquid onto the dry chemical analysis element 12 are performed. Further, the nozzle tip 14, which has been used for the analysis and has been removed from the spotting nozzle 75 at the tip scrapping section 9 located on the element conveyance path R, is allowed to fall so as to pass through the plane of conveyance of the dry chemical analysis element 12 and is scrapped. Therefore, the sections constituting the biochemical analysis apparatus are located so as to overlap one upon another in three dimensions. Accordingly, the size of the entire biochemical analysis apparatus is capable of being kept small.

What is claimed is:

1. A biochemical analysis method, comprising the steps of:
   i) loading a plurality of samples and a plurality of dry chemical analysis elements, which are necessary for analyses of the samples, on a circular sampler tray, having a rotating disk such that, the rotating disk supports the loaded plurality of samples and the dry chemical analysis elements,
   ii) sucking each of the samples, which have been loaded on the sampler tray, with a spotting nozzle unit,
   iii) spotting the sucked sample onto one of the dry chemical analysis elements with the spotting nozzle unit, and
   iv) supporting a plurality of nozzle tips each of which is operable to be fitted to a spotting nozzle of the spotting unit, a plurality of diluent liquid vessels and a plurality of mixing cups by the rotating disk, and
   v) keeping a temperature of each of the dry chemical analysis elements, which have been spotted with the samples, at a constant temperature in an incubator,
   wherein an element conveying member is located within the sampler tray, the element conveying member pushing each of the dry chemical analysis elements from a center side of the rotating disk and thereby conveying each of the dry chemical analysis elements, and
   the rotating disk is provided with a path for the element conveying member besides sections for supporting the plurality of the dry chemical analysis elements.

2. A method as defined in claim 1 further comprising:
   supporting a reference liquid vessel, which accommodates a reference liquid, is non-rotating section in the sample tray, and
   providing an evaporation preventing cover, which opens and closes an opening of the reference liquid vessel, is located in the non-rotating section.

3. A biochemical analysis method, comprising the steps of:
   i) loading a plurality of samples and a plurality of dry chemical analysis elements, which are necessary for analyses of the samples, on a circular sampler tray, having a rotating disk such that, the rotating disk supports the loaded plurality of samples and the dry chemical analysis elements,
   ii) sucking each of the samples, which have been loaded on the sampler tray, with a spotting nozzle unit,
   iii) spotting the sucked sample onto one of the dry chemical analysis elements with the spotting nozzle unit, and
   iv) supporting a plurality of nozzle tips each of which is operable to be fitted to a spotting nozzle of the spotting unit, a plurality of diluent liquid vessels and a plurality of mixing cups by the rotating disk, and
   v) keeping a temperature of each of the dry chemical analysis elements which have been spotted with the samples, at a constant temperature in an incubator, the method further comprising:
   supporting a reference liquid vessel, which accommodates a reference liquid, by a non-rotating section in the sample tray, and
   providing an evaporation preventing cover, which opens and closes an opening of the reference liquid vessel, in the non-rotating section,
   wherein an element conveying member is located within the sampler tray, the element conveying member pushing each of the dry chemical analysis elements from a center side of the rotating disk and thereby conveying each of the dry chemical analysis elements, and
   the rotating disk is provided with a path for the element conveying member besides sections for supporting the plurality of the dry chemical analysis elements.

4. A biochemical analysis method, comprising the steps of:
   i) loading a plurality of samples and a plurality of dry chemical analysis elements, which are necessary for analyses of the samples, on a circular sampler tray,
   ii) sucking each of the samples, which have been loaded on the sampler tray, through a spotting nozzle of a spotting nozzle unit,
   iii) spotting the sucked sample onto one of the dry chemical analysis elements from the spotting nozzle of the spotting nozzle unit, and
   iv) keeping a temperature of each of the dry chemical analysis elements, which have been spotted with the samples, at a constant temperature in an incubator,
   wherein an element conveyance path, along which each of the dry chemical analysis elements is conveyed from the sampler tray to a spotting section for the sample spotting, and a spotting nozzle movement path, along which the spotting nozzle of the spotting nozzle unit is moved, are set on an identical straight line.

5. A method as defined in claim 4 wherein a tip scrapping section for removing a nozzle tip, which has been fitted to the spotting nozzle, from the spotting nozzle is located on an extension of the element conveyance path, and
   the nozzle tip, which has been removed from the spotting nozzle at the tip scrapping section, is allowed to fall so as to pass through a plane of conveyance of the dry chemical analysis element and is scrapped.

6. A biochemical analysis method, comprising the steps of:
- i) loading a plurality of samples and a plurality of dry chemical analysis elements, which are necessary for analyses of the samples, on a circular sampler tray, having a rotating disk such that, the rotating disk supports the loaded plurality of samples and the dry chemical analysis elements,
- ii) sucking each of the samples, which have been loaded on the sampler tray, with a spotting nozzle unit,
- iii) spotting the sucked sample onto one of the dry chemical analysis elements with the spotting nozzle unit, and
- iv) supporting a plurality of nozzle tips each of which is operable to be fitted to a spotting nozzle of the spotting unit, a plurality of diluent liquid vessels and a plurality of mixing cups by the rotating disk, and
- v) keeping a temperature of each of the dry chemical analysis elements, which have been spotted with the samples, at a constant temperature in an incubator,
- vi) keeping a temperature of each of the dry chemical analysis elements, which have been spotted with the samples, at a constant temperature in an incubator,
- wherein an element conveying member is located within the sampler tray, the element conveying member pushing each of the dry chemical analysis elements from a center side of the rotating disk and thereby conveying each of the dry chemical analysis elements, and
- the rotating disk is provided with a path for the element conveying member besides sections for supporting the plurality of the dry chemical analysis elements.

7. A biochemical analysis method, comprising the steps of:
- i) loading a plurality of samples and a plurality of dry chemical analysis elements necessary for analysis of the samples on a circular sampler tray having a rotating disk such that, the rotating disk supports the loaded plurality of samples and the dry chemical analysis elements, each of said dry chemical analysis elements having a code thereon which represents information of type of analysis,
- ii) selecting one of the samples loaded on the sample tray for each dry chemical analysis element in accordance with the information of a type of analysis represented by the code of the dry chemical analysis;
- iii) sucking each of the samples, which have been loaded on the sampler tray, with a spotting nozzle unit,
- iv) spotting the sucked sample onto one of the dry chemical analysis elements with the spotting nozzle unit, and
- v) supporting a plurality of nozzle tips each of which is operable to be fitted to a spotting nozzle of the spotting unit, a plurality of diluent liquid vessels and a plurality of mixing cups by the rotating disk, and
- vi) keeping a temperature of each of the dry chemical analysis elements, which have been spotted with the samples, at a constant temperature in an incubator,
- wherein an element conveying member is located within the sampler tray, the element conveying member pushing each of the dry chemical analysis elements from a center side of the rotating disk and thereby conveying each of the dry chemical analysis elements, and
- the rotating disk is provided with a path for the element conveying member besides sections for supporting the plurality of the dry chemical analysis elements.

* * * * *